United States Patent
Rajendran et al.

(10) Patent No.: US 12,144,821 B1
(45) Date of Patent: Nov. 19, 2024

(54) SELECTIVE 3-PRENYL 5-METHYL ETHER, 7-O-RHAMNOSIDE FLAVONE FOR THE TREATMENT OF HEPATIC CANCER

(71) Applicant: KING FAISAL UNIVERSITY, Al-Ahsa (SA)

(72) Inventors: Peramaiyan Rajendran, Al-Ahsa (SA); Lalitha Keddal Govindaram, Madurai (IN); Basem M. Abdallah, Al-Ahsa (SA); Rajkapoor Balasubramanian, Namakkal (IN); Enas M. Ali, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/431,303

(22) Filed: Feb. 2, 2024

(51) Int. Cl.
*A61K 31/7048* (2006.01)
*A61P 35/00* (2006.01)

(52) U.S. Cl.
CPC .......... *A61K 31/7048* (2013.01); *A61P 35/00* (2018.01)

(58) Field of Classification Search
None
See application file for complete search history.

(56) References Cited

U.S. PATENT DOCUMENTS

2021/0113596 A1 4/2021 Von Maltzahn et al.

FOREIGN PATENT DOCUMENTS

CN 115518096 A 12/2022

OTHER PUBLICATIONS

Forni, Cinzia, et al. "Flavonoids: A myth or a reality for cancer therapy ?. " Molecules 26.12 (2021): 3583.*
Tungmunnithum, Duangjai, et al. "Flavonoids and other phenolic compounds from medicinal plants for pharmaceutical and medical aspects: An overview." Medicines 5.3 (2018): 93.*
Rashid, et al; "Flavonoids and Their Biological Secrets"; Plant and Human Health, vol. 2. Jan. 23, 2019 : 579-605. Published online Jan. 23, 2019. doi: 10.1007/978-3-030-03344-6_24.
Atilaw, et al; "Four Prenylflavone Derivatives with Antiplasmodial Activities from the Stem of *Tephrosia purpurea* subsp. leptostachya"; Molecules. Sep. 2017; 22(9): 1514. Published online Sep. 10, 2017. doi: 10.3390/molecules22091514.
Yin, et al; "Kaempferol 3-O-rhamnoside-7-O-rhamnoside is an endogenous flavonol inhibitor of polar auxin transport in *Arabidopsis* shoots"; New Phytol. Jan. 2014; 201(2): 466-475. Published online Oct. 25, 2013. doi: 10.1111/nph.12558.
Garcia, et al; "Flavonoids Effects on Hepatocellular Carcinoma in Murine Models: A Systematic Review"; Evid Based Complement Alternat Med. 2018; 2018: 6328970. Published online Feb. 28, 2018. doi: 10.1155/2018/6328970.
PubChem 5-methoxy, 3-prenyl 7-O-rhamnopyranosio falvone CID 24205532 Created Feb. 29, 2008.
"Flavonoids"; MedchemExpress.com, Inhibitors, Screening Libraries, Proteins; Accessed on Dec. 11, 2023.

* cited by examiner

*Primary Examiner* — Patrick T Lewis
(74) *Attorney, Agent, or Firm* — Nath, Goldberg & Meyer; Joshua B. Goldberg

(57) ABSTRACT

3-prenyl 5-methyl ether, 7-O-rhamnoside flavone compound, a method of extracting the compound, a pharmaceutical composition comprising said compounds and a suitable carrier, and a method of using the compounds. The 3-prenyl 5-methyl ether, 7-O-rhamnoside flavone is identified as having an antiproliferative effect on cancer cells.

7 Claims, 4 Drawing Sheets

SELECTIVE 3-PRENYL 5-METHYL ETHER, 7-O-RHAMNOSIDE FLAVONE FOR THE TREATMENT OF HEPATIC CANCER

BACKGROUND

1. Field

The present disclosure provides a selective antiproliferative agent, 3-prenyl 5-methyl ether, 7-o-rhamnoside flavone. This compound and compositions thereof are useful as therapeutic agents for preventing growth of cancer cell lines.

2. Description of the Related Art

The prognosis for hepatocellular carcinoma (HCC) is poor because it is usually diagnosed in the advanced stages. In the early stages of the disease, there are no specific symptoms, therefore most HCC patients are diagnosed with an advanced stage of the disease. Globally, it is the fourth leading cause of cancer-related death. Cancer resection and radiotherapy are used to treat HCC patients, but the high rate of metastasis and recurrence after surgery can negatively affect survival rates.

Flavonoids are known to have several medicinal applications due to their anti-inflammatory, anti-oxidative, anti-carcinogenic, neuroprotective, and cardio protective properties.

Thus, there exists a need to develop anticancer agents solving the abovementioned problems.

SUMMARY

The compounds described herein pertain to the field of pharmaceuticals, particularly flavones, the process of synthesis thereof, compositions including these compounds, and the use of the compounds as anticancer agents.

In an effort to develop novel anticancer agents, a novel identified 3-prenyl 5-methyl ether, 7-O-rhamnoside flavone for the treatment of hepatic cancer has been achieved by an extraction method. The compounds showed promising anti-cancer and wound healing activity.

A treatment for cancer comprising an effective amount of a 3-prenyl 5-methyl ether, 7-O-rhamnoside having the formula:

I and a pharmaceutically acceptable carrier.

In an embodiment, the present subject matter relates to a method of treating cancer comprising administering to a subject a pharmaceutically effective amount of the compound of formula I and a pharmaceutically acceptable carrier. Further contemplated herein are pharmaceutical compositions containing these compounds, as well as methods of inhibiting cell growth including cancer cells, including but not limited to liver cancer, by administering the present compounds to a patient in need thereof.

These and other features of the present subject matter will become readily apparent upon further review of the following specification.

DETAILED DESCRIPTION OF THE PREFERRED EMBODIMENTS

Figure 1A:
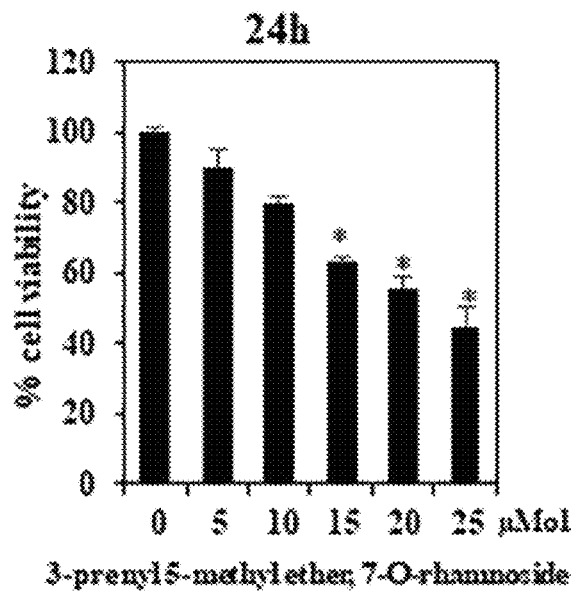
FIG. 1A-1C show the effect of 3-prenyl 5-methyl ether, 7-O-rhamnoside on the proliferation of liver cancer (HepG2) after 24 hours (1A), 48 hours (1B), and 72 hours (1C).

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, iodo, and bromo.

As used herein, "heteroatom" refers to an atom of any element other than carbon or hydrogen and includes, for example, nitrogen, oxygen, silicon, sulfur, phosphorus, and selenium.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer, and healing of wounds.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a treatment for cancer comprising an effective amount of a 3-prenyl 5-methyl ether, 7-O-rhamnoside having the formula:

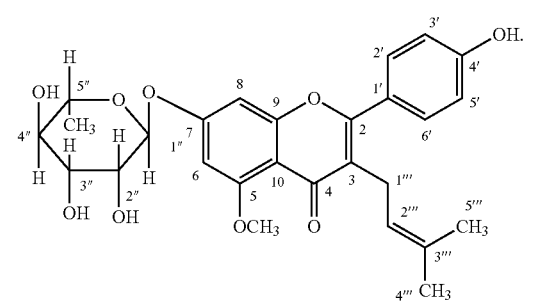

In another embodiment, the present subject matter relates to a method of treating cancer comprising administering to a subject a pharmaceutically effective amount of the compound of formula I and a pharmaceutically acceptable carrier. In one embodiment, the cancer may be hepatic cancer. In other embodiments, the cancer may be liver cancer.

In one embodiment, the present subject matter relates to a method of inhibiting cell growth activity in a subject, comprising administering to a patient in need thereof a therapeutically effective amount of the compound of formula I. In another embodiment, the cancer cells may be from hepatic cancer. In other embodiments, the cancer cells may be liver cancer cells.

In a further embodiment, the present subject matter relates to a method of inhibiting cell growth activity in a subject, comprising administering to a patient in need thereof a therapeutically effective amount of the compound of formula I. The cancer cells may include hepatic cancer cells.

In another embodiment, the present subject matter relates to a method of healing wounds comprising administering to a wound a pharmaceutically effective amount of the compound of formula I and a pharmaceutically acceptable carrier.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; low molecular weight aliphatic esters such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, and precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via the formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general pathway. Ethyl acetate concentrate of *Clerodendrum philippinum* (*C. phlipinum*) is filtered, with the solvents of increasing polarity. Fractions were collected each time.

In another embodiment, the present subject matter is directed to pharmaceutical compositions comprising a therapeutically effective amount of the compounds as described herein, together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one, two, or more of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for the treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods, and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, nontoxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained-release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable nontoxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained-release formulations, and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of nontoxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compounds contained in such parenteral compositions is highly dependent on the specific nature thereof, as well as the activity of the compound and the needs of the subject. However, percentages of the active ingredient of 0.01% to 10% in solution are employable and will be higher if the composition is a solid, which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of cancer. Specifically, the present compounds can be used to inhibit cell growth of cancer cells in a patient.

Accordingly, in an embodiment of the present subject matter, the 3-prenyl 5-methyl ether, 7-O-rhamnoside flavone, as described herein, was engaged in in vitro study against hepatic cancer (as tested in HepG2 cell lines). Cell viability was monitored. Cell migration was monitored. Tumor invasion was also monitored. Values are mean±SD of three independent experiments for each type of assay.

Figure 1B:
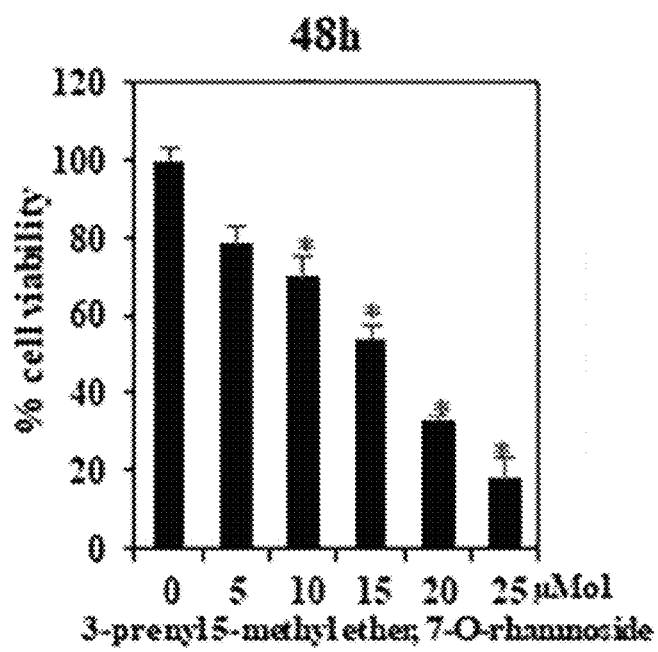
Figure 1C:
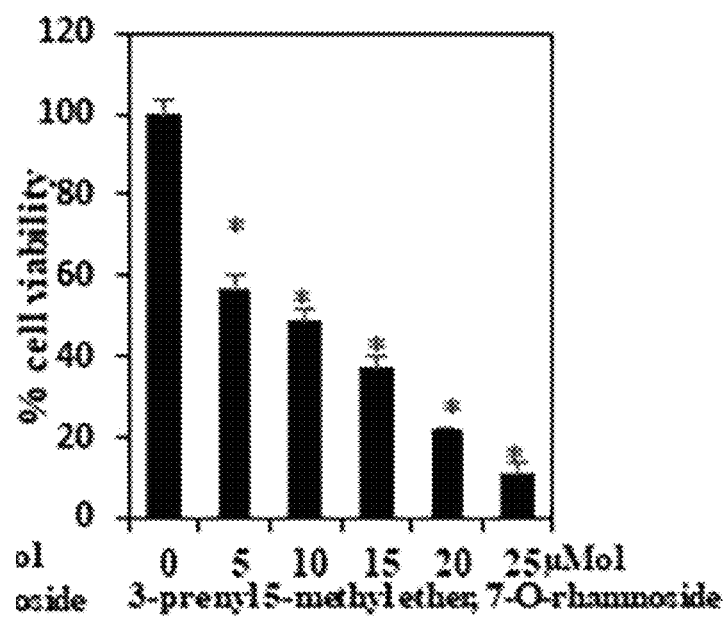

In another embodiment, the potentiation by 3-prenyl 5-methyl ether, 7-O-rhamnoside as dose dependent was examined. Cells were treated with different concentrations of 3-prenyl 5-methyl ether, 7-O-rhamnoside. Potentiation is seen at both 15 and 20 µmol 3-prenyl 5-methyl ether, 7-O-rhamnoside as illustrated in FIGS. 1A-1C. These results also indicated enhancement of anti-proliferative effects of 3-prenyl 5-methyl ether, 7-O-rhamnoside.

The metastatic cascade of carcinomas, tumor migration and invasion is the first and most important steps. It involves profound changes in cell adhesion, allowing tumor cells to dissociate and migrate from the primary site.

In a further embodiment, the invasion effects of 3-prenyl 5-methyl ether, 7-O-rhamnoside based on these data in hepatic cancer (HepG2) cells at non-cytotoxic concentrations were studied. Several essential steps of metastasis, including migration (FIGS. 2A-2B) and invasion (FIGS. 3A-3B) of human liver cancer cells, are inhibited by the 3-prenyl 5-methyl ether, 7-O-rhamnoside. These findings suggested that 3-prenyl 5-methyl ether, 7-O-rhamnoside treatment had an anti-migratory/invasive effect on HepG2 cells.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one, two, or more of the present compounds are used, or one of the present compounds is used. Similarly, one or more of the present compounds can be used in combination therapy with one or more additional active agents.

The following examples relate to various methods of manufacturing certain specific compounds as described herein.

EXAMPLES

Example 1

General Procedure for Extracting 3-prenyl 5-methyl ether, 7-O-rhamnoside flavone Ethyl acetate concentrate (20 gm) of *C. phlippinum* was chromatographed in silicagel (60-120 mesh, 400 gms, 100×5 cm) column, using gradient elution with the solvents of increasing polarity. Fractions of 50 ml were collected each time. And the residue was examined on TLC with suitable solvents. The details of the fractions are given in Table 1.

TABLE 1

Chromatographic fractionation of the ethyl acetate concentrate of *C. phlippinum*

| Fractions collected | Eluent composition | Remarks |
|---|---|---|
| 1-10 | 100% $C_6H_6$ | Waxy substance |
| 11-55 | 90/10 to 30/70 $C_6H_6$/ EtOAc | Non isolable solid |
| 56-75 | 40/60 $C_6H_6$/ EtOAc | Yellow solid |
| 76-100 | 50/50 $C_6H_6$/ EtOAc | Non isolable solid |

The pale yellow solid, obtained by concentrating the eluent fractions 56-75, responded positively for flavonoid glycoside to ferric chloride test (green coloration) and gave yellow coloration when fumed with ammonia (characteristic of polyphenolics), it gave pink coloration in Shinoda's test, and violet coloration with Molisch's reagent characteristic of a flavonoid glycoside). The solid was found to be pure when tested on PC and the $R_f$ value are given Table 2. It was designated as CL taken up for characterization by UV, $^1$H NMR, 13C NMR and EI-MS spectra. EI-MS of CL gave mass spectral lines at m/z 352, 324, 284, 186, 166, 121 and 69.

TABLE 2

$R_f$(×100) values of CL in PC

| | Solvent system | | | | | | |
|---|---|---|---|---|---|---|---|
| Compound | 15% AcOH | 30% AcOH | 50% AcOH | 60% AcOH | BAW | Forestal | PhOH |
| CL | 18 | 36 | 79 | 84 | 21 | 86 | 48 |
| Aglycone | 11 | 31 | 50 | 66 | 88 | 82 | 91 |

Acid Hydrolysis of CL:

CL was subjected acid hydrolytic studies to find out the nature of sugar and aglycone. The concentrate of aqueous layer obtained from CL was compared on PC with various authentic samples on Whatman No. 1 filter paper and using aniline hydrogen phthalate as the spray reagent. The sugar was identified to be rhamnose and the aglycone was characterized as apigenin derivative.

CL was obtained as amorphous yellowish solid from menthol (melting point 137±1° C.; yield 40 mg). The UV spectrum in MeOH exhibited characteristic $\lambda_{max}$ value for band I at 333 nm and band II at 268 nm, which indicated the flavine nature of it (Table 3). A bathochromic shift of band I (+53 nm) on addition of NaOMe suggested the presence of hydroxyl at C-4'. Nonappearance of new peak at 300-310 nm in the NaOAc indicates the absence of free OH at C-7. Further the absence of NaOAc shift of band II also indicated that C-7 was not free. Absence of bathochromic shift of band I on addition of NaOAc and $H_3BO_3$ suggested the absence of ortho dihydroxy group in ring B. No characteristic shift of band I with AlCl$_3$ and also addition of HCL with AlCl$_3$ suggested absence of 5-OH in ring A.

TABLE 3

λ$_{max}$ values of CL

| Shift reagents | λ$_{max}$ value (nm) |
|---|---|
| MeOH | 268, 333 |
| +NaOMe | 245sh, 269, 301sh, 386 |
| +NaOAc | 256sh, 267, 355 |
| +NaOAc/H$_3$BO$_3$ | 267, 340 |
| +AlCl$_3$ | 276, 300, 348 |
| +AlCl$_3$/HCL | 227, 299, 341 |

Also, the absence of signal at 12-14 ppm in $^1$H NMR suggested the position of —OCH$_3$ at C-5 (Table 4). I aromatic region a set of doublets of two protons each appeared at δ 7.88 ppm (2H, d, J=8.5 Hz) and δ 6.94 ppm (2H, d, J=8.5 Hz) corresponding to H-2'/H-6' and H-3'/H-5' and this is typical of A$_2$B$_2$ pattern of four protons in ring B with an oxygenated substituent at C-4' (Table 4).

TABLE 4

$^1$H NMR data of CL

| Chemical shift values δ H (ppm) | Signal assignment |
|---|---|
| 9.4 | 1H, s, 4'—OH |
| 7.88 | 2H, d, J = 8.5 Hz, H-2'/6' |
| 6.94 | 2H, d, J = 8.5 Hz, H-3'/5' |
| 6.41 | 1H, d, J = 2.5 Hz, H-8 |
| 6.36 | 1H, d, J = 2.5 Hz, H-6 |
| 5.30 | 1H, t, H-2''' |
| 5.15 | 1H, d, J = 2 Hz, anomeric H-1'' |
| 3.78 | 3H, methoxy protons |
| 3.6-3.2 | Sugar protons |
| 3.11 | 2H, d, J = 7 Hz, H-1 |
| 1.28 | 6H, s, H-4''', H-5''' |
| 1.02 | 3H, d, J = 6.5 Hz, H-6 |

In $^{13}$C NMR spectrum of CL, the signal at δ 56.1 ppm (Table 5) was assigned to methoxyl group. The presence of methoxyl proton was further confirmed by the proton signal at δ 3.78 ppm in $^1$H NMR. The signal at δ 9.4 ppm accounts for the presence of 4'—OH group. The compound did not answer the Horhammer Hansel test and Wilson's boric acid test [12], which were indicative of the absence of free OH at C-3 and C-5.

A meta coupled doublet at δ 6.41 ppm (1H, d, J-2.5 Hz) and δ 6.36 ppm (1H, d, J=2.5 Hz) corresponding to H-8 and H-6 protons suggesting 5,7 di-substitution in ring A, which was supported by the $^{13}$C NMR and EI-MS.

The sugar residue of CL was found to be rhamnose by hydrolytic studies, the signals displayed at δ 1.02 (3H, d, J=6.5 Hz, H-6''), 5.15 PPM (1H, d, J=2 Hz, H-1'') in $^1$H NMR and δ 17.3 ppm (C-6) in $^{13}$C NMR clearly revealed the rhamnoside nature of the glycoside[14].

The downfield shift to prenyl protons δ 1.28 (6H, H-4''', H-5''') 15, 3.11 (H-1''') and 5.3 ppm (H-2''') indicated the presence of prenyl group in CL. The carbon signals at δ 28.3 (C-1'''), 122.5 (C-2'''), 131.5 (C-3'''), 23.2 (C-4''') and 18.8 ppm (C-5''') and appearance of C-3 at δ 117.4 ppm confirmed the position of prenyl at C-3. [17]

The introduction of OCH$_3$ group to the C-5 in apigenin caused the signals due to C-2, C-3, C-4, C-5, C-6, C-7, C-8, C-9, C-10, C-1', C-2', C-3', C-4', C-5' and C-6' to shift −3.5, +13, −6.3, −1.5, −1.9, −2.4, +2.1, +1.7, +2.4, +0.3, −1.2, −0.4, 0.6, −0.4 and −1.9 ppm respectively. The introduction of rhamnose to the 7-OH of apigenin caused the upfield shift of C-7 and downfield shift of ortho and para related positions C-6, C-7, C-8 and C-10. Finally, the (M+) ion at m/z 352 and fragments at m/z 324, 284, 186, 166, 121 and 69 indicated the attachment of one hydroxyl, one prenyl and one methoxyl groups in the CL.

Thus based on the R$_f$R$_f$ values, UV, 1H NMR, 13C NMR, and EI-MS studies, the structure of CL has been characterized as apigenin 3-prenyl 5-methyl ether, 7-O-rhamnoside. This is the first report of methoxylated flavonoid glycoside in this plant.

Pharmacological Activity

Example 2

Antiproliferative Screening
Cell Culture and Culture Media

Cells (HepG2) were provided from the American Type Culture Collection (ATCC) unless otherwise stated. Cells were grown in ATCC-formulated specific DMEM/F12 medium for each cell line with supplements of 5% fetal bovine serum, 10 U/ml penicillin, 10 μg/ml streptomycin, and 4% glutamine. All cell lines were placed in a humidified incubator a 37° C. in an atmosphere of 5% CO2 and 95% air. Cells were cultured into two groups. One as control cells and the other as cell lines treated for one day (3-prenyl 5-methyl ether, 7-O-rhamnoside-treated cells).

TABLE 5

$^{13}$C NMR data of CL

| C | C-2 | C-3 | C-4 | C-5 | C-6 | C-7 | C-8 | C-9 | C-10 |
|---|---|---|---|---|---|---|---|---|---|
| δ ppm | 162.0 | 117.3 | 176.9 | 160.5 | 98.4 | 162.5 | 97.7 | 160.4 | 107.5 |

| C | C-1' | C-2' | C-3' | C-4' | C-5' | C-6' |
|---|---|---|---|---|---|---|
| δ ppm | 123.0 | 128.6 | 116.9 | 161.1 | 116.9 | 127.9 |

| C | C-1'' | C-2'' | C-3'' | C-4'' | C-5'' | C-6'' |
|---|---|---|---|---|---|---|
| δ ppm | 99.6 | 70.4 | 70.1 | 71.8 | 69.9 | 17.3 |

| C | C-1''' | C-2''' | C-3''' | C-4''' | C-5''' | OCH$_3$ |
|---|---|---|---|---|---|---|
| δ ppm | 28.36 | 122.5 | 131.5 | 23.2 | 18.8 | 56.1 |

Cell Viability Assay

The cell viability will be tested using MTT. The cells will be maintained in wells of a 12-well plate within 4×105 cells/well population and will be exposed to 0,5,10,15,20 and 25 μmol 3-prenyl 5-methyl ether, 7-O-rhamnoside for 24, 48 and 72 hrs. After treatment, cells were incubated with 400 μL of 0.5 mg/mL of MTT in PBS for 2 h. The culture supernatant was removed, the remaining MTT formazan crystals was dissolved in 400 μL of DMSO, and the absorbance was measured at 570 nm using an ELISA micro-plate reader (Bio-Tek Instruments, Winooski, VT, USA). The effect of 3-prenyl 5-methyl ether, 7-O-rhamnoside on cell viability was assessed as the percentage of viable cells compared with the vehicle-treated control cells, which were arbitrarily designated as 100%.

Preliminary in vitro study found that 3-prenyl 5-methyl ether, 7-O-rhamnoside, were potentially cytotoxic for the HepG2 cancer cell line (FIGS. 1A-1C). Whether the potentiation by 3-prenyl 5-methyl ether, 7-O-rhamnoside was dose dependent was examined. For this cells were treated with different concentrations of 3-prenyl 5-methyl ether, 7-O-rhamnoside. As can be seen in FIG. 1, potentiation can be seen at both 15 and 20 μmol 3-prenyl 5-methyl ether, 7-O-rhamnoside. These results also indicated enhancement of anti proliferative effects of 3-prenyl 5-methyl ether, 7-O-rhamnoside.

As illustrated in FIG. 1, the effect of 3-prenyl 5-methyl ether, 7-O-rhamnoside on the proliferation of liver cancer (HepG2). The cells were treated with increasing concentrations of 3-prenyl 5-methyl ether, 7-O-rhamnoside, (0-5, 10, 15, 20 and 25 μmol/mL for 24,48 and 72 h. The viability was assessed using the MTT assay. Values are mean±SD of three independent experiments. (p<0.01 compared untreated cells).

Example 3

Migration and Invasion Study

During the metastatic cascade of carcinomas, tumor migration and invasion is the first and most important steps. It involves profound changes in cell adhesion, allowing tumour cells to dissociate and migrate from the primary site. We evaluated the invasion effects 3-prenyl 5-methyl ether, 7-O-rhamnoside based on these data in hepatic cancer (HepG2) cells at non-cytotoxic concentrations. Several essential steps of metastasis, including migration (FIGS. 2A-2B) invasion (FIG. 3A-3B) of human liver cancer cells, are inhibited by the 3-prenyl 5-methyl ether, 7-O-rhamnoside. These findings suggested that 3-prenyl 5-methyl ether, 7-O-rhamnoside treatment had an anti-migratory/invasive effect on HepG2 cells.

Figure 2A:
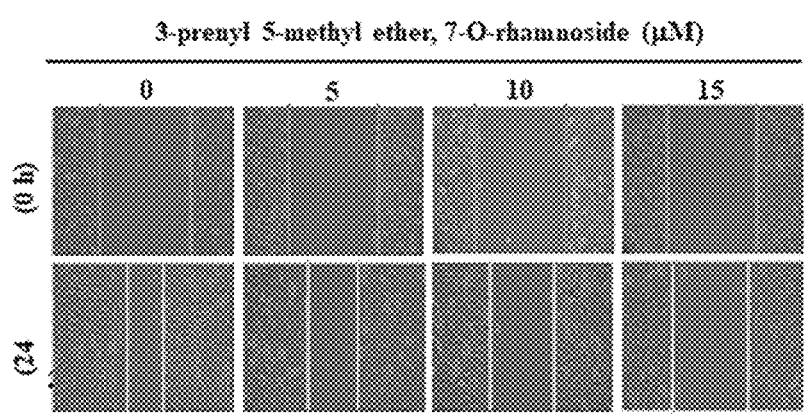
FIGS. 2A and 2B show photographs (2A) and a graph (2B) of results of a migration assay.
Figure 2B:
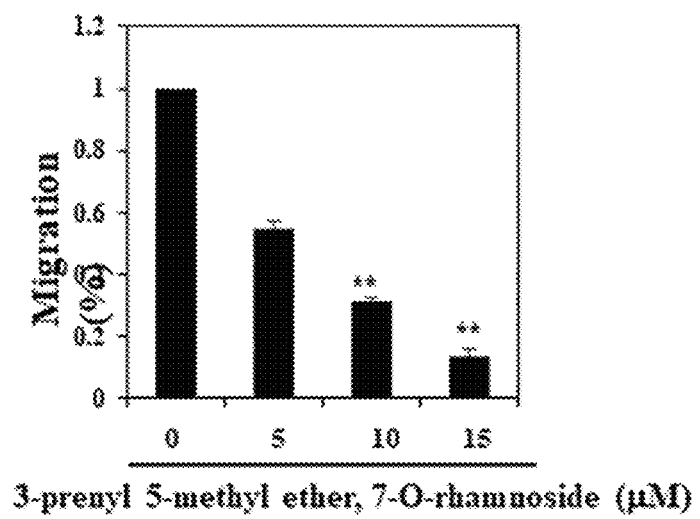

The migration and invasion assays were conducted by photographing the cells that migrated the membrane (200× magnification). As illustrated in FIGS. 2A-2B HepG2 cells were treated with 3-prenyl 5-methyl ether, 7-O-rhamnoside at indicated doses for 24 hours. The percentage inhibition of migrating cells was quantified and expressed based on untreated cells (control) represented 100%. The migration was determined by the areas of the wound closure calculated from three microscopic fields per sample.

Figure 3A:
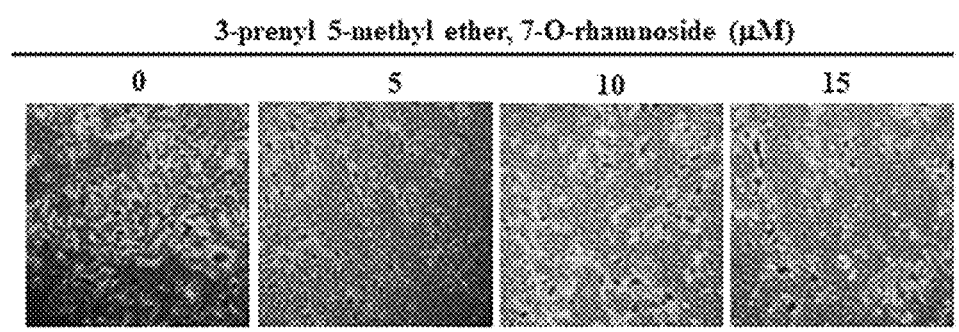
FIGS. 3A and 3B show photographs (3A) and a graph (3B) of results of a invasion assay.
Figure 3B:
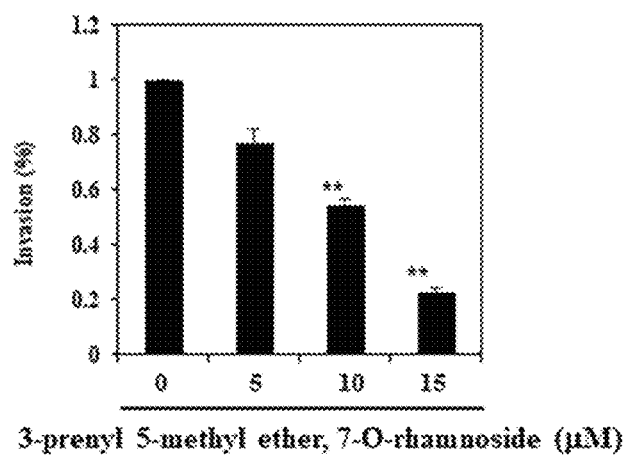

As illustrated in FIGS. 3A-3B, invasiveness was determined by counting cells in three microscopic fields per sample. The inhibitory percentage of invading cells was quantified and expressed with untreated cells (control) representing 100%. Values are mean±SD of three independent experiments. (p<0.01 compared untreated cells).

It is to be understood that selective 3-prenyl 5-methyl ether, 7-O-rhamnoside flavones are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating cancer in a subject, the method comprising administering to a subject in need thereof a therapeutically effective amount of a pharmaceutical composition comprising an effective amount of an apigenin 3-prenyl 5-methyl ether, 7-O-rhamnoside having the formula I:

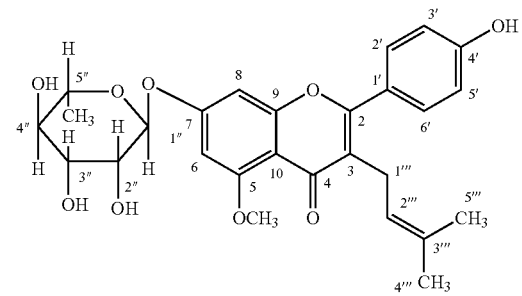

and a pharmaceutically acceptable carrier.

2. A method of inhibiting cell growth activity in a subject, the method comprising administering to a subject in need thereof a pharmaceutical composition comprising a therapeutically effective amount of an apigenin 3-prenyl 5-methyl ether, 7-O-rhamnoside having the formula I:

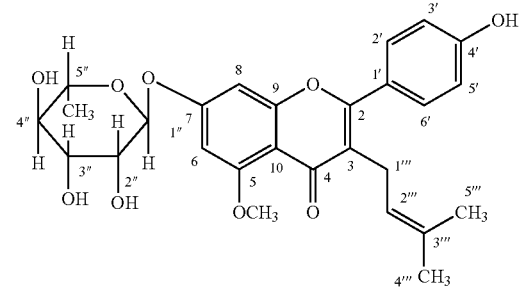

and a pharmaceutically acceptable carrier.

3. The method of treating cancer in a subject of claim 1, the method comprising inhibiting cell growth of cancer cells in the subject.

4. The method of inhibiting cell growth of cancer cells in a subject of claim 3, wherein the cancer cells are from hepatic cancer.

5. A method of healing a wound in a subject comprising administering to a subject in need thereof a therapeutically effective amount of a pharmaceutical composition comprising an effective amount of an apigenin 3-prenyl 5-methyl ether, 7-O-rhamnoside having the formula I:

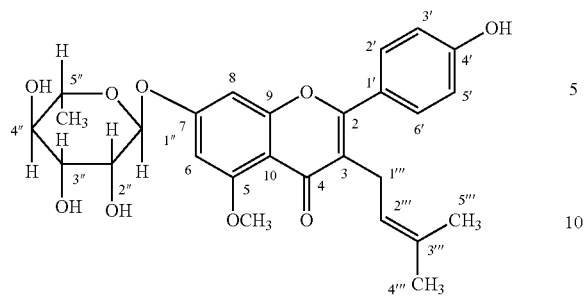
and a pharmaceutically acceptable carrier.
6. The method of healing a wound in a patient of claim 5, wherein the pharmaceutical composition is administered to the wound.
7. The method of treating cancer of claim 1, wherein the cancer is liver cancer.
\* \* \* \* \*